(12) United States Patent
Gerlitz

(10) Patent No.: US 8,219,169 B2
(45) Date of Patent: Jul. 10, 2012

(54) APPARATUS AND METHOD USING LIGHT RETRO-REFLECTED FROM A RETINA TO NON-INVASIVELY MEASURE THE BLOOD CONCENTRATION OF A SUBSTANCE

(75) Inventor: Jonathan Gerlitz, Herzliya (IL)

(73) Assignee: GlucoVista Inc., Fairfield, NJ (US)

( * ) Notice: Subject to any disclaimer, the term of this patent is extended or adjusted under 35 U.S.C. 154(b) by 1155 days.

(21) Appl. No.: 12/029,342

(22) Filed: Feb. 11, 2008

(65) Prior Publication Data
US 2009/0201490 A1    Aug. 13, 2009

(51) Int. Cl.
*A61B 5/1455*    (2006.01)
(52) U.S. Cl. ....................... 600/318; 600/319
(58) Field of Classification Search .................. 600/318, 600/319
See application file for complete search history.

(56) References Cited

U.S. PATENT DOCUMENTS

| | | | |
|---|---|---|---|
| 3,958,560 A | 5/1976 | March | |
| 4,014,321 A | 3/1977 | March | |
| 4,877,322 A | 10/1989 | Hill | |
| 5,222,496 A | 6/1993 | Clarke et al. | |
| 5,318,022 A | 6/1994 | Taboada et al. | |
| 5,433,197 A | 7/1995 | Stark | |
| 5,523,883 A | 6/1996 | Myers et al. | |
| 5,560,356 A | 10/1996 | Peyman | |
| 5,743,262 A | 4/1998 | Lepper et al. | |
| 5,774,213 A | 6/1998 | Trebino et al. | |
| 5,776,060 A | 7/1998 | Smith et al. | |
| 5,820,557 A | 10/1998 | Hattori et al. | |
| 5,882,301 A | 3/1999 | Yoshida | |
| 5,885,224 A | 3/1999 | Yoshida | |
| 6,134,458 A | 10/2000 | Rosenthal | |
| 6,152,875 A * | 11/2000 | Hakamata | ..................... 600/319 |

(Continued)

FOREIGN PATENT DOCUMENTS
EP    0792619 A1    9/1997
(Continued)

OTHER PUBLICATIONS

PCT International Search Report, App. No. PCT/IB02/03774, dated Mar. 21, 2003.

(Continued)

*Primary Examiner* — Eric Winakur
(74) *Attorney, Agent, or Firm* — Parsons Behle & Latimer

(57) ABSTRACT

A method determines the concentration of a substance in a subject's blood. The method includes noninvasively irradiating an eye with a measurement light beam having a first wavelength and a first power and with a reference light beam having a second wavelength and a second power. The second wavelength is different from the first wavelength. The method further includes measuring at least one of a body temperature of the subject and an ambient temperature of the subject. The method further includes detecting a power of the measurement retro-reflected light beam and detecting a power of the reference retro-reflected light beam. The method further includes calculating a measurement ratio of the detected power of the measurement retro-reflected light beam and the first power and calculating a reference ratio of the detected power of the reference retro-reflected light beam and the second power. The method further includes calculating a parameter dependent on the measurement ratio and the reference ratio and determining a concentration of the substance in the subject's blood in response to the calculated parameter and to the at least one of the body temperature and the ambient temperature.

28 Claims, 9 Drawing Sheets

U.S. PATENT DOCUMENTS

| | | |
|---|---|---|
| 6,181,957 B1 | 1/2001 | Lambert et al. |
| 6,226,089 B1 | 5/2001 | Hakamata |
| 6,305,804 B1 | 10/2001 | Rice et al. |
| 6,424,850 B1 | 7/2002 | Lambert et al. |
| 6,477,394 B2 | 11/2002 | Rice et al. |
| 6,494,576 B1 | 12/2002 | L'Esperance, Jr. |
| 6,574,501 B2 | 6/2003 | Lambert et al. |
| 6,853,854 B1 | 2/2005 | Proniewicz et al. |
| 6,895,264 B2 | 5/2005 | Rice et al. |
| 6,958,039 B2 | 10/2005 | Burd et al. |
| 6,968,222 B2 | 11/2005 | Burd et al. |
| 6,975,892 B2 | 12/2005 | Burd et al. |
| 6,998,247 B2 | 2/2006 | Monfre et al. |
| 7,039,446 B2 | 5/2006 | Ruchti et al. |
| 7,271,912 B2 * | 9/2007 | Sterling et al. .............. 356/436 |
| 2002/0049389 A1 | 4/2002 | Abreu |
| 2006/0015022 A1 | 1/2006 | Cho et al. |

FOREIGN PATENT DOCUMENTS

| | | | |
|---|---|---|---|
| GB | 2409033 A | | 6/2005 |
| JP | S60-236631 U1 | | 11/1985 |
| JP | H05-176917 A | | 7/1993 |
| JP | H09-234190 A | | 9/1997 |
| JP | H09-308623 A | | 12/1997 |
| WO | WO 93/07801 A | | 4/1993 |
| WO | WO 00/57218 | | 9/2000 |
| WO | WO03/012486 | * | 2/2003 |
| WO | WO 2004/060154 A9 | | 7/2004 |

OTHER PUBLICATIONS

International Search Report and Written Opinion for PCT/US2009/032057, mailed Jan. 4, 2009.

International Search Report and Written Opinion for PCT/US2009/032056, mailed May 4, 2009.

* cited by examiner

APPARATUS AND METHOD USING LIGHT RETRO-REFLECTED FROM A RETINA TO NON-INVASIVELY MEASURE THE BLOOD CONCENTRATION OF A SUBSTANCE

CROSS-REFERENCE TO RELATED APPLICATIONS

This application is related to U.S. patent application Ser. No. 12/029,339, entitled "Apparatus and Method for Non-Invasive Measurement of the Concentration of a Substance in a Subject's Blood," filed on even date herewith.

BACKGROUND OF THE INVENTION

1. Field of the Invention

This application relates generally to devices and methods for non-invasively measuring the concentration of a substance in a subject's blood, and more particularly, to devices and methods for non-invasively measuring the concentration of glucose in the subject's blood.

2. Description of Related Art

Numerous systems were suggested in the last decades, to solve the problem of non-invasively measuring the level of substances (e.g., glucose) in a subject's blood. The main drawback of all those systems was a very poor signal to noise ratio, which required a very heavy computing system, and resulted in inconsistent and unrepeatable results.

In addition, conventional systems for non-invasive measurement of substances (e.g., glucose) in the blood do not take into consideration the various parameters that affect such measurements in human tissue. For example, conventional systems that utilize measurements taken from the eye do not take into consideration the changing parameters of the eye, such as pupil size, other materials of the eye, the absorption or scattering of light inside the eyeball. In particular, U.S. Pat. Nos. 6,494,576 and 5,820,557 suggest subtracting the reflected light intensity from the intensity of the originally irradiated light and to correlate this subtracted value to glucose concentration.

SUMMARY OF THE INVENTION

In certain embodiments, a method determines the concentration of a substance in a subject's blood. The method comprises noninvasively irradiating an eye of the subject with a measurement light beam having a first wavelength and a first power. At least a portion of the measurement light beam is retro-reflected from the retina of the eye, thereby producing a measurement retro-reflected light beam having the first wavelength. The method further comprises noninvasively irradiating the eye of the subject with a reference light beam having a second wavelength and a second power. The second wavelength is different from the first wavelength. At least a portion of the reference light beam is retro-reflected from the retina of the eye, thereby producing a reference retro-reflected light beam having the second wavelength. The method further comprises measuring at least one of a body temperature of the subject and an ambient temperature of the subject. The method further comprises detecting a power of the measurement retro-reflected light beam. The method further comprises detecting a power of the reference retro-reflected light beam. The method further comprises calculating a measurement ratio of the detected power of the measurement retro-reflected light beam and the first power. The method further comprises calculating a reference ratio of the detected power of the reference retro-reflected light beam and the second power. The method further comprises calculating a parameter dependent on the measurement ratio and the reference ratio. The method further comprises determining a concentration of the substance in the subject's blood in response to the calculated parameter and to the at least one of the body temperature and the ambient temperature.

In certain embodiments, an apparatus measures a concentration of a substance in a subject's blood. The apparatus comprises at least one light source generating light having a first wavelength and generating light having a second wavelength. The second wavelength is different from the first wavelength. The apparatus further comprises an optical system which directs at least a portion of the light having the first wavelength towards the subject's eye as a measurement light beam having a first power. At least a portion of the measurement light beam is retro-reflected from the subject's retina. The optical system directs at least a portion of the light having the second wavelength towards the subject's eye as a reference light beam having a second power. At least a portion of the reference light beam is retro-reflected from the subject's retina. The apparatus further comprises a detector system receiving the retro-reflected portion of the measurement light beam and the retro-reflected portion of the reference light beam. The detector system is responsive to the received retro-reflected portion of the measurement light beam by generating a first signal indicative of the power of the received retro-reflected portion of the measurement light beam. The detector system is responsive to the received retro-reflected portion of the reference light beam by generating a second signal indicative of the power of the received retro-reflected portion of the reference light beam. The apparatus further comprises at least one temperature detector which measures at least one of a body temperature of the subject and an ambient temperature of the subject and which generates at least one signal indicative of the at least one of the body temperature and the ambient temperature. The apparatus further comprises a computing system which receives the first signal, the second signal, and the at least one signal. The computing system calculates a first ratio of the first power and the power of the received retro-reflected portion of the measurement light beam. The computing system calculates a second ratio of the second power and the power of the received retro-reflected portion of the reference light beam. The computing system calculates a parameter dependent on the first ratio and the second ratio, and determines a concentration of the substance in the subject's blood in response to the calculated parameter and to the at least one signal.

In certain embodiments, a computing system measures a concentration of a substance in a subject's blood. The computing system comprises one or more inputs configured to receive a first signal indicative of a first power of a measurement light beam incident on a subject's eye, a second signal indicative of a second power of a reference light beam incident on a subject's eye, a third signal indicative of a third power of a portion of the measurement light beam retro-reflected from the subject's retina, a fourth signal indicative of a fourth power of a portion of the reference light beam retro-reflected from the subject's retina, and at least one signal indicative of at least one of a body temperature of the subject and an ambient temperature of the subject. The measurement light beam has a first wavelength and the reference light beam has a second wavelength different from the first wavelength. The computing system further comprises an electric circuit configured to calculate a first ratio of the first power and the third power. The electric circuit is further configured to calculate a second ratio of the second power and the fourth power. The electric circuit is further configured to calculate a parameter dependent on the first ratio and the second ratio. The electric circuit is further configured to determine a concentration of the substance in the subject's blood in response to the calculated parameter and to the at least one of a body temperature of the subject and an ambient temperature of the subject.

In certain embodiments, a method determines the concentration of a substance in a subject's blood. The method comprises measuring an interaction of at least one light beam with a portion of the subject's body. The method further comprises calculating a value of an optically-measured parameter indicative of the interaction of the at least one light beam with the substance in the portion of the subject's body. The method further comprises measuring values of one or more temperature-indicative parameters corresponding to a temperature of the portion of the subject's body. The method further comprises accessing an empirical correlation of the optically-measured parameter and the one or more temperature-indicative parameters to concentrations of the substance in blood. The method further comprises obtaining a concentration of the substance in the subject's blood using the empirical correlation. The concentration corresponds to the value of the optically-measured parameter and the values of the one or more temperature-indicative parameters.

In certain embodiments, a method determines a correlation of a concentration of a substance in a person's blood with a plurality of parameters. The method comprises invasively measuring values of the concentration of the substance in the blood of a plurality of people at a plurality of conditions. The plurality of people is statistically representative of a larger population of people. The method further comprises non-invasively optically measuring values of a parameter from the plurality of people at the plurality of conditions. The value of the optically-measured parameter measured from a portion of a person's body is indicative of the concentration of the substance in the person's blood. The method further comprises measuring values of one or more temperature-indicative parameters for the plurality of people at the plurality of conditions. The one or more temperature-indicative parameters corresponds to a temperature of the portion of the person's body. The method further comprises generating a correlation by correlating the measured values of the optically-measured parameter and the measured values of the one or more temperature-indicative parameters to the measured values of the concentration of the substance in the blood of the plurality of people.

DETAILED DESCRIPTION

Figure 1:
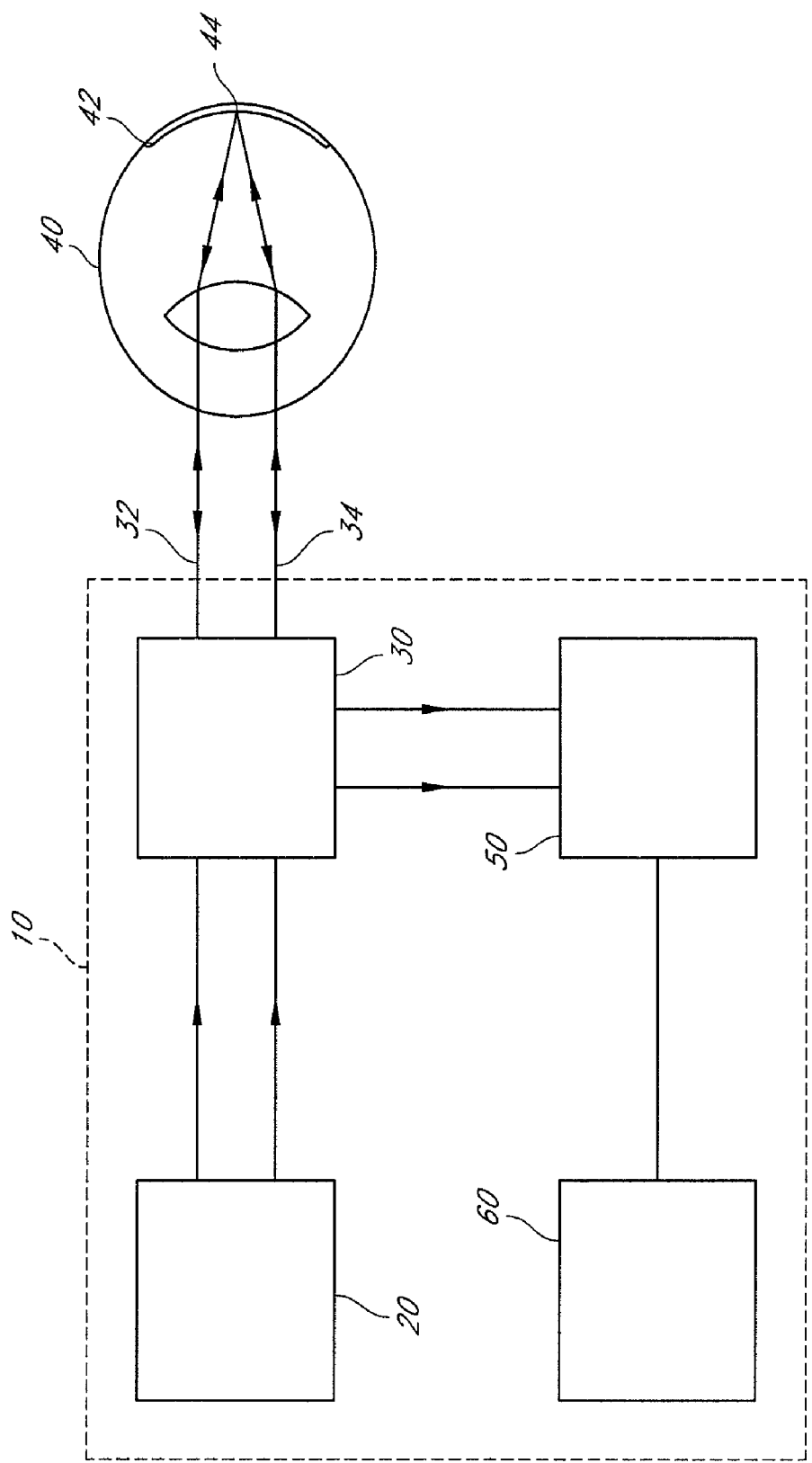
FIG. 1 schematically illustrates an example configuration of an apparatus in accordance with certain embodiments described herein.

As described more fully below, the simple subtraction scheme utilized in the conventional systems of the prior art fails to account for other parameters which affect the concentration measurements of substances in the subject's body. Thus, these simple subtraction schemes cannot reliably be used as measures of the substance concentration of the subject's blood.

Certain embodiments described herein provide an apparatus and a measurement and calculation method to isolate a measurable parameter that can be correlated to the concentration of substances (e.g., glucose) in the subject's blood. As described more fully below, in certain embodiments, the method includes constraints on (i) the wavelengths and relationships between the wavelengths of the light being used; and (ii) the method of calculations based on measurements with these wavelengths in order to eliminate or otherwise account for various parameters that may affect the measurements but are not relevant to the actual concentrations of the substances (e.g., glucose) being measured.

While certain embodiments are described herein in the context of measuring glucose concentrations, concentrations of other substances which can be measured in accordance with certain embodiments described herein include, but are not limited to, cholesterol. While certain embodiments are described herein in the context of infrared or near-infrared optical absorption measurements, other near-infrared optical measurements which can be improved in accordance with certain embodiments described herein include, but are not limited to, transmission measurements, reflection measurements, scattering measurements, polarization measurements, and Raman measurements. While certain embodiments are described herein in the context of non-invasive optical measurements taken from the subject's eye, other non-invasive optical measurements which can be improved in accordance with certain embodiments described herein are taken from other portions of the subject's body including, but not limited to, skin, earlobe, finger (web or cuticle), lip, or cheek.

Certain embodiments described herein advantageously provide a non-invasive glucose meter which has a good signal to noise ratio, thus making the measurement consistent, repeatable and reliable. Certain embodiments described herein advantageously provide such an apparatus for non-invasive glucose measurement, which is easy and simple to handle by the user, small sized and inexpensive. Certain embodiments described herein advantageously provide a non-invasive glucose meter which can be used in various environments, indoors and outdoors.

Certain embodiments described herein utilize the properties of the eye as an optical apparatus. Every optical apparatus, which is equipped with focusing means and a focal plane, shows the phenomenon of retro-reflection, meaning that the apparatus reflects back at least a portion of the entering light beam in the same direction it comes from. Certain embodiments described herein provide an electro-optical apparatus which uses the retro-reflection characteristic of the eye in order to determine the concentration of glucose or of another substance in the eye liquid (the vitreous body) and/or in the blood.

FIG. 1 schematically illustrates an example apparatus 10 in accordance with certain embodiments described herein. The apparatus 10 comprises at least one light source 20 which generates light having a first wavelength. The at least one light source 20 further generates light having a second wavelength. The apparatus 10 further comprises an optical system 30 which directs at least a portion of the light having the first wavelength towards the subject's eye 40 as a measurement light beam 32 having a first power, at least a portion of the measurement light beam 32 retro-reflecting from the subject's retina 42. The optical system 30 also directs at least a portion of the light having the second wavelength towards the subject's eye 40 as a reference light beam 34 having a second power, at least a portion of the reference light beam 34 retro-reflecting from the subject's retina 42. The apparatus 10 further comprises a detector system 50 which receives the retro-reflected portion of the measurement light beam 32 and the retro-reflected portion of the reference light beam 34. The detector system 50 is responsive to the received retro-reflected portion of the measurement light beam 32 by generating a first signal indicative of the power of the received retro-reflected portion of the measurement light beam 32. The detector system 50 is responsive to the received retro-reflected portion of the reference light beam 34 by generating a second signal indicative of the power of the received retro-reflected portion of the reference light beam 34. The apparatus 10 further comprises a computing system 60 which receives the first signal and the second signal from the detector system 50. The computing system 60 calculates a first ratio of the first power and the power of the received retro-reflected portion of the measurement light beam 32. The computing system 60 further calculates a second ratio of the second power and the power of the received retro-reflected portion of the reference light beam 34. The computing system 60 further calculates a parameter dependent on the first ratio and the second ratio (e.g., a difference of the first ratio and the second ratio or a difference between a logarithm of the first ratio and a logarithm of the second ratio) and determines a concentration of the substance in the subject's blood in response to the calculated parameter.

In certain embodiments, the apparatus 10 is sized to be portable and easily held by a user (e.g., a medical practitioner or the subject themself). As described more fully below, the apparatus 10 can comprise an internal power supply (e.g., battery or fuel cell) and can comprise a display (e.g., liquid-crystal display) to receive signals indicative of the concentration values from the computing system 60 and to present information regarding the concentration values (e.g., the concentration values themselves or indications that the concentration values are above or below a predetermined value) to the user. The apparatus 10 can also comprise a memory system (e.g., flash memory, dynamic random-access memory) configured to receive signals indicative of information regarding the concentration values from the computing system 60 and to store information for later use or for display to the user. In certain embodiments, the computer system 60 can comprises the display and/or the memory system.

In certain embodiments, the apparatus 10 is configured to be positioned at a distance of at least 100 millimeters from the subject's eye during operation (e.g., while the measurement light beam 32 and the reference light beam 34 are directed towards the subject's retina 42). In certain other embodiments, the apparatus 10 is configured to be positioned such that the optical pathlength of the retro-reflected portion of the measurement light beam 32 and the retro-reflected portion of the reference light beam 34 from the subject's eye 40 to the detector system 50 is at least 100 millimeters. The optical pathlength from the subject's eye 40 to the detector system 50 for certain embodiments is sufficiently long such that the detector system 50 receives mainly the retro-reflected portions of the measurement light beam 32 and the reference light beam 34, and advantageously avoids receiving other reflections (e.g., from the subject's cornea) which the apparatus 10 could interpret to be noise.

Figure 2:
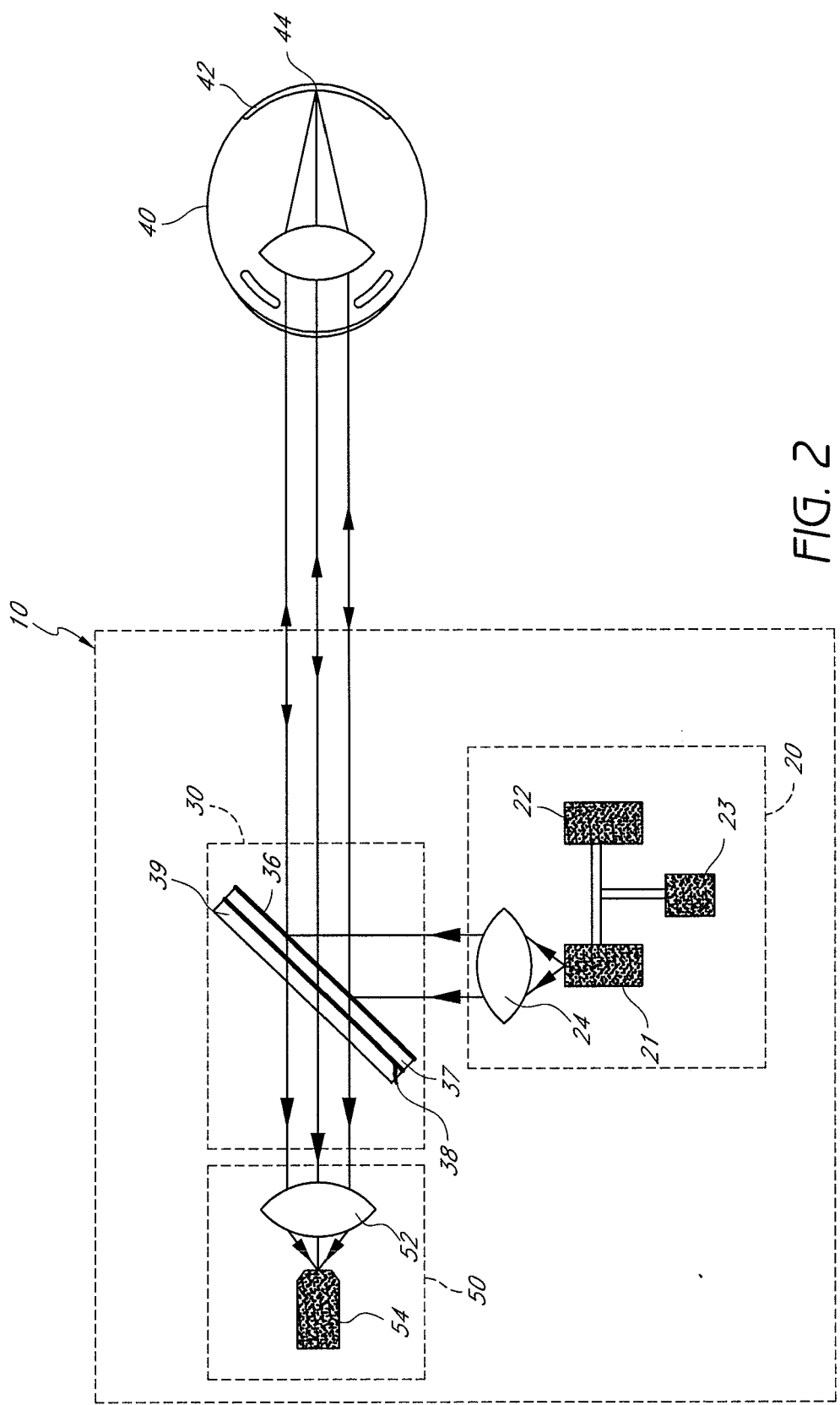
FIG. 2 schematically illustrates an example configuration of an apparatus having a first light source and a second light source coupled to a movable element in accordance with certain embodiments described herein.

The at least one light source 20 is configured to output light having the first wavelength to the optical system 30 and to output light having the second wavelength to the optical system 30. In certain embodiments, the at least one light source 20 comprises at least two infrared (IR) emitters which emit light within two different wavelength bands. For example, FIG. 2 schematically illustrates an example apparatus 10 having a first light source 21 and a second light source 22 in accordance with certain embodiments described herein. Examples of light sources compatible with certain embodiments described herein include, but are not limited to, a light bulb with a bandpass filter, a laser diode, and a high power infrared light emitting diode.

In the apparatus 10 schematically illustrated by FIG. 2, the first light source 21 and the second light source 22 are coupled to a movable element 23 (e.g., a motor) which can be actuated to position either the first light source 21 or the second light source 22 so as to transmit light to the optical system 30. Thus, in certain such embodiments, the measurement light beam 32 and the reference light beam 34 are directed towards the subject's eye 40 sequentially, one after the other. In certain embodiments, the light having the first wavelength and the light having the second wavelength propagate towards the optical system 30 along the same path as one another, as schematically illustrated by FIG. 2. In certain embodiments, the at least one light source 20 comprises at least one optical element 24 (e.g., lens) which directs light from the at least one light source 20 towards the optical system 30.

Figure 3:
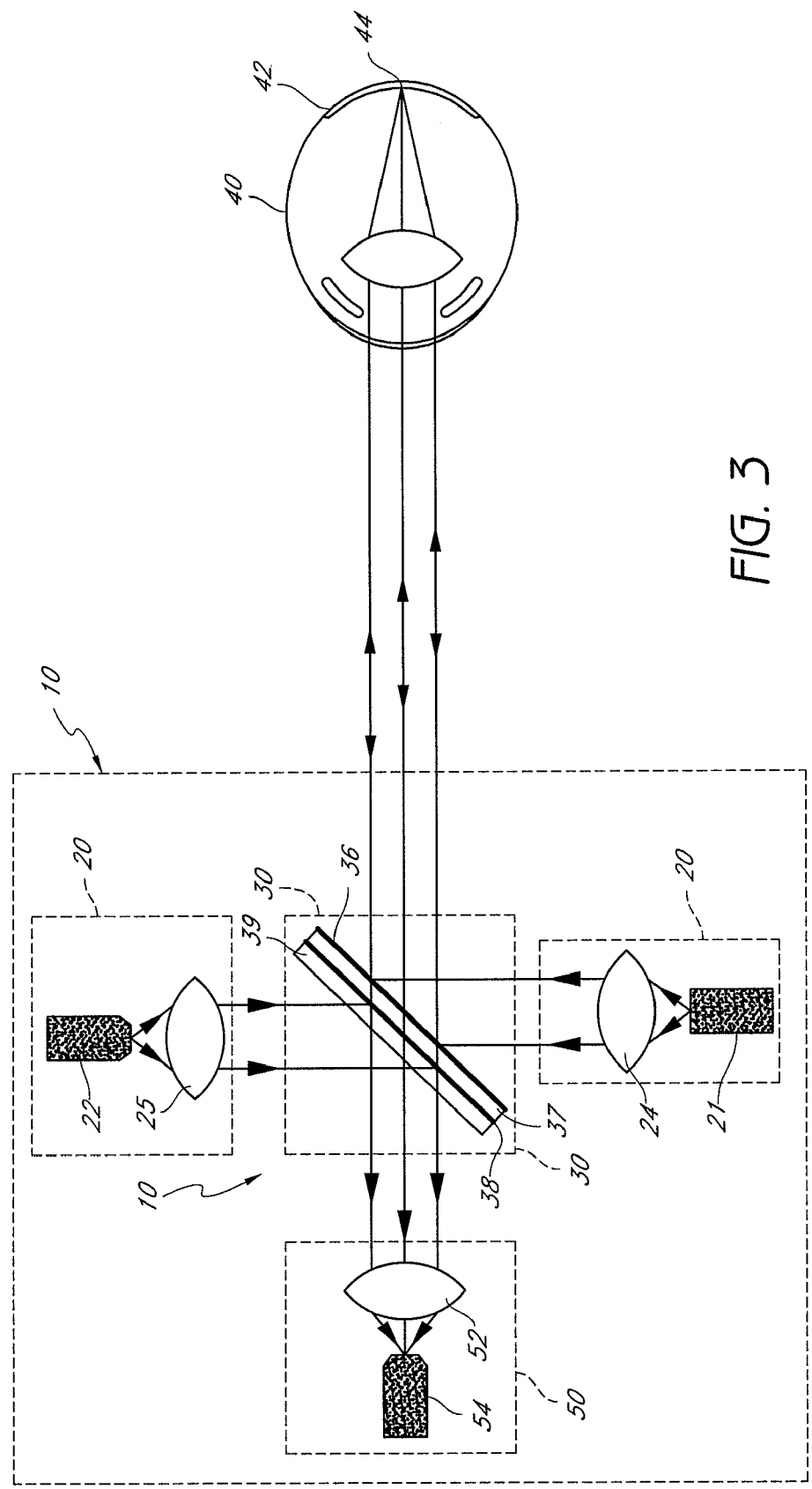
FIG. 3 schematically illustrates an example configuration of an apparatus having a first light source and a second light source spaced from one another in accordance with certain embodiments described herein.

In the apparatus 10 schematically illustrated by FIG. 3, the first light source 21 and the second light source 22 are spaced from one another but are each positioned to transmit light to the optical system 30. Thus, in certain such embodiments, the measurement light beam 32 and the reference light beam 34 are directed towards the subject's eye 40 concurrently with one another. In certain embodiments, the light having the first wavelength and the light having the second wavelength propagate towards the optical system 30 along different paths which can be parallel or non-parallel to one another. For example, the first light source 21 and a corresponding optical element 24 (e.g., lens) are positioned on one side of the optical system 30, and the second light source 22 and a corresponding optical element 25 are positioned on another side of the optical system 30. Other configurations of the first light source 21, the second light source 22, and optical elements of the at least one light source 20 are also compatible with certain embodiments described herein.

Figure 4:
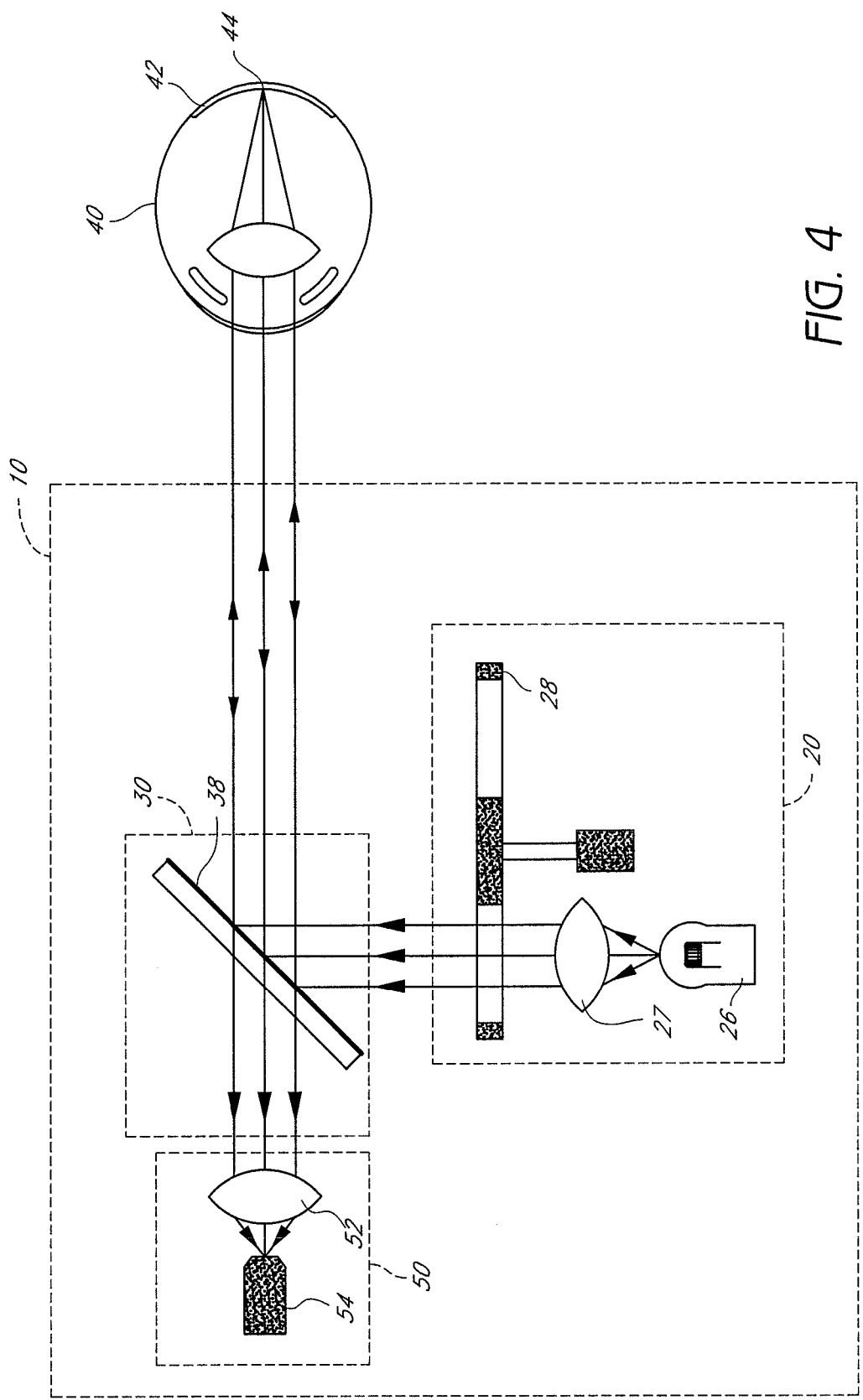
FIG. 4 schematically illustrates an example configuration of an apparatus having a single wide band light source in accordance with certain embodiments described herein.

In certain embodiments, as schematically illustrated by FIG. 4, the at least one light source 20 comprises a single wideband light source 26 (e.g., a miniature lamp) which emits light in a wide wavelength band, an optical element 27 (e.g., lens), and a filter wheel 28 comprising two or more narrow band filters which filter the light from the wide band light source 26 into two different wavelength bands. Certain such embodiments are advantageously used for providing more than two wavelengths to analyze the concentrations of glucose or other substances. In certain embodiments, the filter wheel 28 comprises a motor which can be actuated to position a selected filter of the filter wheel 28 in the path of the light from the wideband light source 26, thereby filtering out selected wavelengths from the light emitted by the at least one light source 20. While FIG. 4 schematically illustrates an embodiment in which the optical element 27 is between the wideband light source 26 and the filter wheel 28, in certain other embodiments, the filter wheel 28 is between the wideband light source 26 and the optical element 27.

In certain embodiments, the light emitted by the at least one light source 20 having the first wavelength comprises a light beam (e.g., a nearly parallel, substantially parallel, or collimated light beam) which the optical system 30 directs towards the subject's eye 40 as the measurement light beam 32, and the light emitted by the at least one light source 20 having the second wavelength comprises a light beam (e.g., a nearly parallel, substantially parallel, or collimated light beam) which the optical system 30 directs towards the subject's eye 40 as the reference light beam 34. In certain other embodiments, the light emitted by the at least one light source 20 comprises a non-parallel or non-collimated light beam, but the optical system 30 is configured to receive the light having the first wavelength and to generate a nearly parallel, substantially parallel, or collimated measurement light beam 32 and to receive the light having the second wavelength and to generate a nearly parallel, substantially parallel, or collimated reference light beam 34. In certain various embodiments, the measurement light beam 32 has a beam divergence less than or equal to 5 degrees, less than or equal to 3 degrees, or less than or equal to 1 degree. In certain various embodiments, the reference light beam 34 has a beam divergence less than or equal to 5 degrees, less than or equal to 3 degrees, or less than or equal to 1 degree. In certain embodiments, the measurement light beam 32 and the reference light beam 34 are substantially parallel to one another. In certain embodiments, the measurement light beam 32 and the reference light beam 34 are parallel to one another such that an angle between the two beams is less than or equal to 0.1 degree. In certain embodiments, the measurement light beam 32 and the reference light beam 34 are substantially co-linear with one another. For example, the measurement light beam 32 and the reference light beam 34 of certain embodiments are parallel to one another and spaced from one another by less than 0.2 millimeter.

In certain embodiments, the first wavelength is in a range of wavelengths in which the substance to be measured (e.g., glucose) has a high absorption coefficient, and the second wavelength is in a range of wavelengths in which the substance to be measured has a low absorption coefficient. In certain embodiments, the first wavelength is in the infrared (IR) or near-infrared (near-IR) range of wavelengths, and the second wavelength is in the infrared (IR) or near-infrared (near-IR) range of wavelengths. In certain various embodiments in which glucose is measured, the first wavelength can be selected to be in a range between about 920 nanometers and about 980 nanometers (e.g., 950 nanometers), in a range between about 1130 nanometers and about 1190 nanometers (e.g., 1160 nanometers), or in a range between about 1.3 microns and about 1.5 microns (e.g., 1460 nanometers). In certain various embodiments in which glucose is measured, the second wavelength is selected to be close to the first wavelength, but having substantially no absorption due to glucose. For example, in certain embodiments in which the first wavelength is in a range between about 920 nanometers and about 980 nanometers, the second wavelength can be in a range between about 800 nanometers and about 905 nanometers (e.g., 870 nanometers or 880 nanometers). In another example, in certain embodiments, the first wavelength is about 1160 nanometers and the second wavelength is about 1120 nanometers. To measure concentrations of other substances in the subject's eye liquid and/or blood, other wavelengths are advantageously used. In certain embodiments, the reference light beam 34 is used as a reference beam which can be used to compensate for changes of the pupil and/or iris, and thus enables the use of the apparatus 10 in various light conditions.

In certain embodiments, the optical system 30 receives light from the at least one light source 20 and directs the measurement light beam 32 and the reference light beam 34 towards the subject's eye 40. In certain embodiments, the optical system 30 is located in the center of the apparatus 10. FIGS. 2 and 3 schematically illustrate an example optical system 30 in accordance with certain embodiments described herein. The optical system 30 of FIGS. 2 and 3 comprises a dichroic coating layer 36, an optical glass layer 37, a holographic beam splitter layer 38, and a cover glass layer 39. This combination of four layers operates in certain embodiments as an optical combiner. The dichroic coating layer 36 of certain embodiments is applied on at least one surface of the optical glass layer 37. In certain embodiments, the dichroic coating layer 36 has a center wavelength corresponding to the wavelength of the first light source 21 or corresponding to the wavelength of the second light source 22. The dichroic coating layer 36 of certain embodiments enables 50-60% of the IR light from the at least one light source 20 to pass through, and 40-50% of the IR light from the at least one light source 20 to be reflected at a 90° angle towards the subject's eye 40.

In certain embodiments, the holographic beam splitter layer 38 is on the other surface of the optical glass layer 37 and is covered by the cover glass layer 39. The holographic beam splitter layer 38 of certain embodiments has a center wavelength corresponding to the wavelength of the first light source 21 or the second light source 22. In certain embodiments, the holographic beam splitter layer 38 allows 50-60% of the light from the at least one light source 20 having the center wavelength to pass through, and 40-50% of the light from the at least one light source 20 having the center wavelength to be reflected at a 270° angle towards the subject's eye 40.

In certain embodiments, the optical system 30 comprises only a single dichroic coating layer 36. For example, in certain such embodiments, the first light source 21 and the second light source 22 change position to emit light towards the optical system 30 intermittently (e.g., by actuating a movable element or motor 23 to move the first light source 21 and the second light source 22 as in FIG. 2). The dichroic coating layer 36 of certain such embodiments is a wide band coating for the wavelengths of both the first light source 21 and the second light source 22.

In certain embodiments, the at least one light source 20 comprises optical elements (e.g., lenses 24, 25) such that the measurement light beam 32 is a nearly parallel, substantially parallel, or collimated beam and the reference light beam 34 is a nearly parallel, substantially parallel, or collimated beam. In certain other embodiments, the optical system 30 comprises optical elements (e.g., lenses) such that the measurement light beam 32 is a nearly parallel, substantially parallel, or collimated beam and the reference light beam 34 is a nearly parallel, substantially parallel, or collimated beam. In certain embodiments, the measurement light beam 32 and the reference light beam 34 are on the same optical path as one another. In certain embodiments, the measurement light beam 32 and the reference light beam 34 each have a diameter (e.g., the full-width-at-half-maximum diameter) of about 2 millimeters. In certain embodiments, the measurement light beam 32 and the reference light beam 34 each have a generally Gaussian beam intensity profile and have a substantially circular or substantially elliptical beam spot shape. In certain embodiments, the measurement light beam 32 and the reference light beam 34 are continuous-wave beams, while in certain other embodiments, the measurement light beam 32 and the reference light beam 34 are pulsed light beams.

The measurement light beam 32 and the reference light beam 34 are directed towards and enter the subject's eye 40 by passing through the cornea, the pupil and/or the iris, the eye lens, and the eye liquid. The two light beams 32, 34 are focused approximately on the retina 42 at a focal point 44. A portion of the measurement light beam 32 is reflected from the retina 42, and a retro-reflected portion of this reflected light comes out of the subject's eye 40 from the same focal point 44 on the exact optical path of the incoming measurement light beam 32, but in the opposite direction. This retro-reflected portion of the measurement light beam 32 propagates towards, and is received by, the apparatus 10. Similarly, a portion of the reference light beam 34 is reflected from the retina 42, and a retro-reflected portion of this reflected light comes out of the subject's eye 40 from the same focal point 44 on the exact optical path of the incoming reference light beam 34, but in the opposite direction. This retro-reflected portion of the reference light beam 34 propagates towards, and is received by, the apparatus 10.

Each of the retro-reflected portion of the measurement light beam 32 and the retro-reflected portion of the reference light beam 34 in certain embodiments passes twice through the eye 40, first through the cornea, the eye lens, and liquid (vitreous body), then focuses on the retina 42, and subsequently is reflected back through the eye liquid, lens, and cornea towards the optical system 30.

In certain embodiments, the retro-reflected portion of the measurement light beam 32 and the retro-reflected portion of the reference light beam 34 are received by the detector system 50 directly from the eye 40. In certain other embodiments, the optical system 30 receives the retro-reflected portion of the measurement light beam 32 and the retro-reflected portion of the reference light beam 34 directly from the eye 40 and transmits these retro-reflected portions to the detector system 50. As schematically illustrated by FIGS. 2, 3, and 4, the detector system 50 is located on the same optical path as the measurement and reference light beams 32, 34 such that the retro-reflected portion of the measurement light beam 32 and the retro-reflected portion of the reference light beam 34 pass through the components of the optical system 30 (e.g., through the beam splitter layer 38) to the detector system 50. For example, in certain embodiments, 50-60% of the retro-reflected portions of the measurement and reference light beams 32, 34 can pass through the beam splitter layer 38 to the detector system 50.

In certain embodiments, the detector system 50 comprises at least one optical element 52 (e.g., lens) and at least one light detector 54. As schematically illustrated by FIGS. 2, 3, and 4, the at least one optical element 52 of certain embodiments receives the retro-reflected light and focuses the retro-reflected light onto the at least one light detector 54. The at least one light detector 54 of certain embodiments is configured to generate a first signal indicative of the power of the received retro-reflected portion of the measurement light beam 32 and to generate a second signal indicative of the power of the received retro-reflected portion of the reference light beam 34. Examples of light detectors compatible with certain embodiments described herein include, but are not limited to, silicon detectors, PbS detectors, or any other kind of IR detector known in the art.

Figure 5:
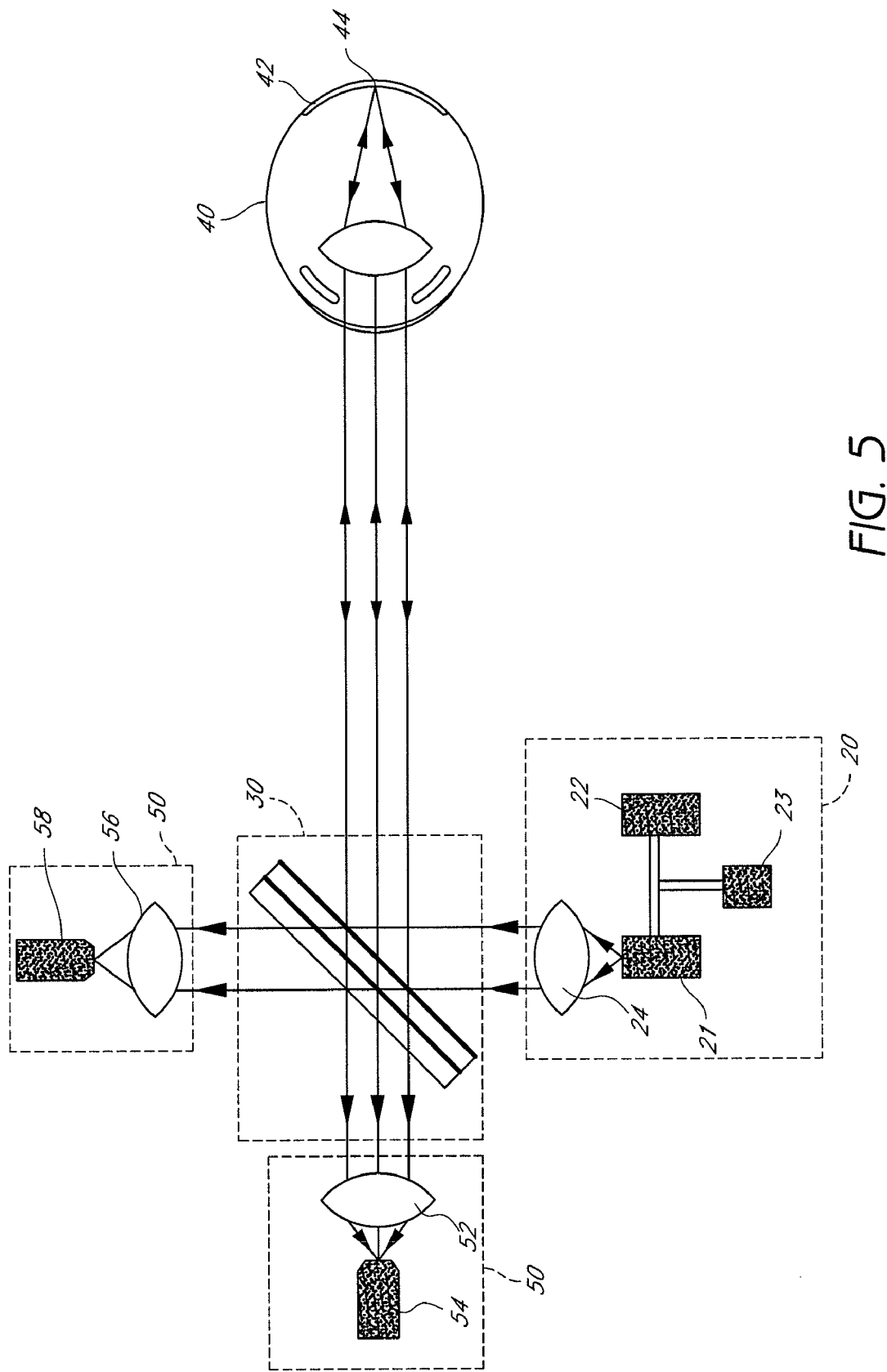
FIG. 5 schematically illustrates an example configuration of an apparatus having two light detectors in accordance with certain embodiments described herein.

FIG. 5 schematically illustrates an example configuration of an apparatus having two optical elements 52, 56 and two light detectors 54, 58 in accordance with certain embodiments described herein. The optical element 52 and the light detector 54 receive the two retro-reflected light beams and the light detector 54 is configured to generate signals corresponding to the powers of the retro-reflected light beams. The optical element 56 and the light detector 58 receive a portion of the light generated by the at least one light source 20 and the light detector 58 is configured to generate signals corresponding to the powers of the measurement and reference light beams 32, 34 incident on the subject's eye 40. Certain such embodiments provide measurements of the power of the incident light beams to compare to the power of the retro-reflected light beams. Other configurations of the at least one light source 20, the optical system 30, and the detection system 50 are also compatible with certain embodiments described herein.

Figure 6:
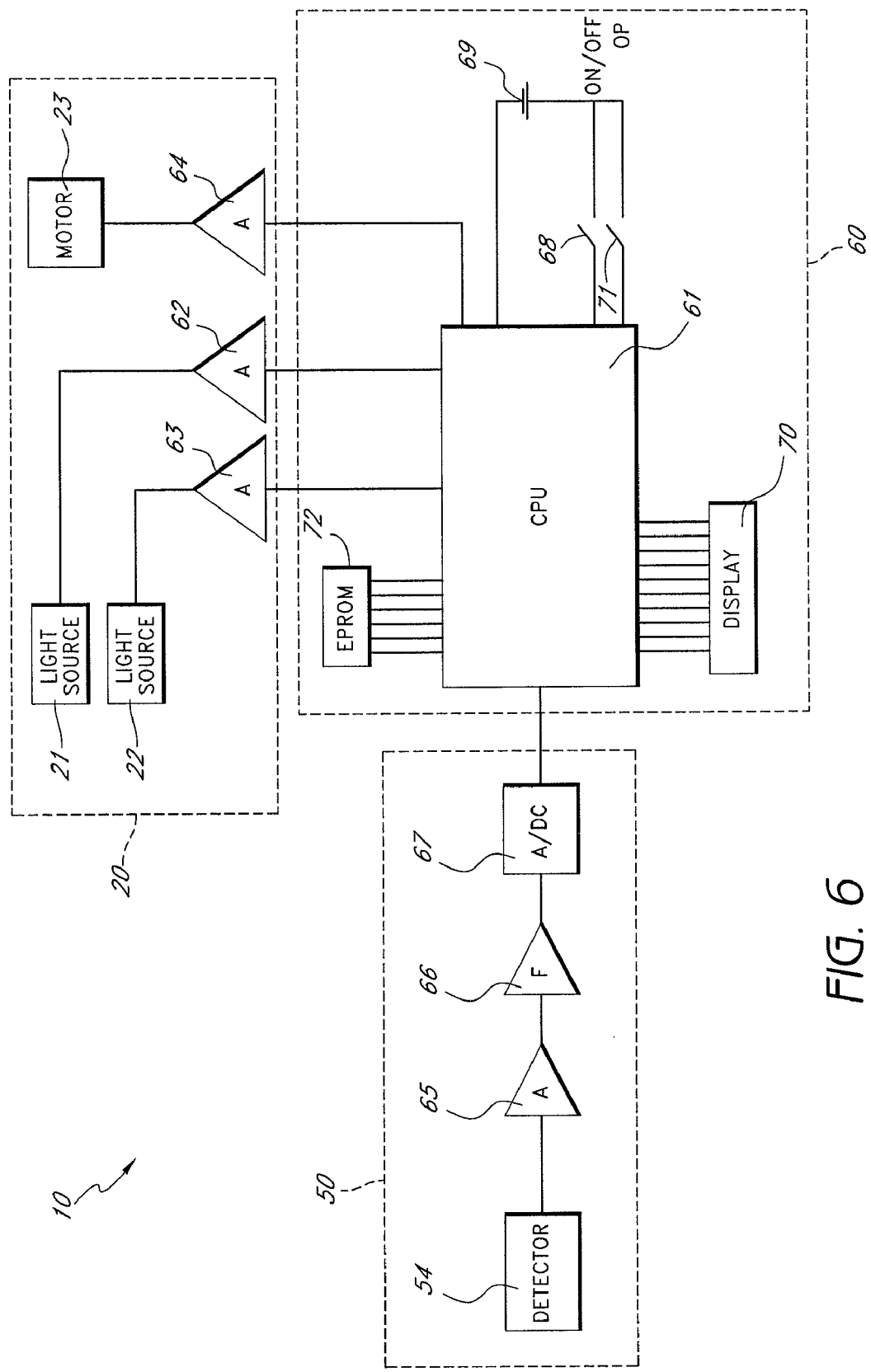
FIG. 6 schematically illustrates an example electronic circuit in accordance with certain embodiments described herein.

FIG. 6 schematically illustrates an electronic diagram of an example apparatus 10 in accordance with certain embodiments described herein. In certain embodiments, the computing system 60 comprises a central processing unit (CPU) 61 (e.g., an Epson 6200, produced by Epson, Japan). The CPU 61 of certain embodiments is electrically coupled to one or more of the at least one light source 20, the optical system 30, and the detector system 50 to control the operation of the apparatus 10.

In certain embodiments, the at least one light source 20 comprises the first light source 21, the second light source 22, a first amplifier 62 electrically coupled to the first light source 21, and a second amplifier 63 electrically coupled to the second light source 22, as schematically illustrated by FIG. 6. The first amplifier 62 and the second amplifier 63 receive signals from the computing system 60 and, in response, activate the first and second light sources 21, 22 (e.g., sequentially or concurrently). In certain embodiments, the at least one light source 20 further comprises a movable element 23 (e.g., motor) and a third amplifier 64 electrically coupled to the movable element 23, as schematically illustrated by FIG. 6. The third amplifier 64 receives signals from the computing system 60 and, in response, activates the movable element 23 so as to position the first and second light sources 21, 22 for transmitting light to the optical system 30.

In certain embodiments, the detector system 50 comprises at least one light detector 54, an amplifier 65, a filter 66, and an analog-to-digital (A/D) converter 67, as schematically illustrated by FIG. 6. For example, in certain embodiments, the A/D converter 67 comprises a fast 12-bit converter. Analog signals from the at least one light detector 54 corresponding to the detected powers of the retro-reflected portions of the measurement light beam 32 and the reference light beam 34 are amplified, filtered, converted to digital signals, and transmitted to the computing system 60. In certain embodiments in which the detector system 50 comprises a second light detector 58 (e.g., as schematically illustrated by FIG. 5), signals from the second light detector 58 corresponding to the power of the incident light beams are amplified, filtered, and converted into digital signals in a similar way. These digital signals can then be used by the computing system 60 as described further herein.

In certain embodiments, the apparatus 10 is turned on by switch 68, which connects the power source 69 (e.g., a lithium battery) to the circuitry. After a self-check, the CPU 61 of certain embodiments displays "Ready" on a display unit 70

(e.g., a liquid crystal display (LCD)). In certain embodiments, to perform a measurement, switch 71 is activated, and, in response, the CPU 61 starts a measurement procedure. In certain embodiments, the CPU 71 activates in sequence the first light source 21 through the first amplifier 62 and the second light source 22 through the second amplifier 63, and activates the movable element 23 through the third amplifier 64 in certain embodiments in which such a movable element 23 is used. The retro-reflected portions of the measurement light beam 32 and the reference light beam 34 detected from the eye 40 are translated by the at least one light detector 54 (e.g., an IR detector) to an analog voltage signal, which is amplified by amplifier 65 and filtered by filter 66. This analog signal is converted to a digital form by the A/D converter 67 and is received and stored by the CPU 71 (e.g., in memory 72). After receiving measurement data corresponding to the two wavelengths, the CPU 71 calculates the concentration of the substance (e.g., glucose) according to the absorption level calculated using calibration parameters stored in the memory 72 (e.g., electrically-erasable programmable read-only memory or E²PROM). The CPU 71 of certain embodiments also transmits signals to the display 70 to make the results of the calculation available to the user.

The absorption of the light beams 32, 34 due to substances within the eye 40 having non-negligible absorption coefficients $\alpha_\lambda$ at the wavelengths of the measurement or reference light beams 32, 34, correlates to the exponential of $(\alpha_\lambda x)$, where x is the optical pathlength within the eye 40. Thus, the magnitude of the absorption is proportional to $$\int_{\lambda_1}^{\lambda_2} e^{\alpha_\lambda x} d\lambda$$

where x is the length of the optical path through the absorbing medium and $\alpha_\lambda$ is the absorption coefficient of the substance (e.g., glucose) to be measured at wavelength $\lambda$.

In certain embodiments, due to the long optical pathlength within the eye 40, the absorption can be significant even in a low concentration of the substance being measured (e.g., glucose). Because the light beams pass through the eye 40 twice, the optical path in the absorbing medium is long, and the absorption signal correlating to the exponential of $(\alpha_\lambda x)$ will be much stronger than in conventional systems which do not primarily use the retro-reflected portions of the light beams. By using the retro-reflected light from the eye, which travels through a long optical path in the absorbing medium, certain embodiments described herein advantageously overcome the main drawback of all previous suggested systems, and inherently have a good signal to noise ratio. The apparatus 10 of certain embodiments is quite simple, as described herein, and due to the good signal to noise ratio, the processing of the signal is also simple and inexpensive.

Certain embodiments described herein advantageously provide improved determinations of the concentration of a substance in a subject's blood using non-invasive optical measurements in conjunction with measurements of other parameters (e.g., temperature) that may affect the measurements of the concentration of the substances (e.g., glucose). In certain embodiments, a method of determining the concentration of a substance in a subject's blood comprises measuring an interaction of at least one light beam with a portion of the subject's body, and calculating a value of an optically-measured parameter indicative of the interaction of the at least one light beam with the portion of the subject's body. The method of certain embodiments further comprises non-invasively measuring values of one or more temperature-indicative parameters corresponding to a temperature of the portion of the subject's body. The method of certain embodiments further comprises accessing an empirical correlation of the optically-measured parameter and the one or more temperature-indicative parameters to concentrations of the substance in blood. The method of certain embodiments further comprises obtaining a concentration of the substance in blood from the empirical correlation. The concentration corresponds to the value of the optically-measured parameter and the values of the one or more temperature-indicative parameters.

Figure 7:
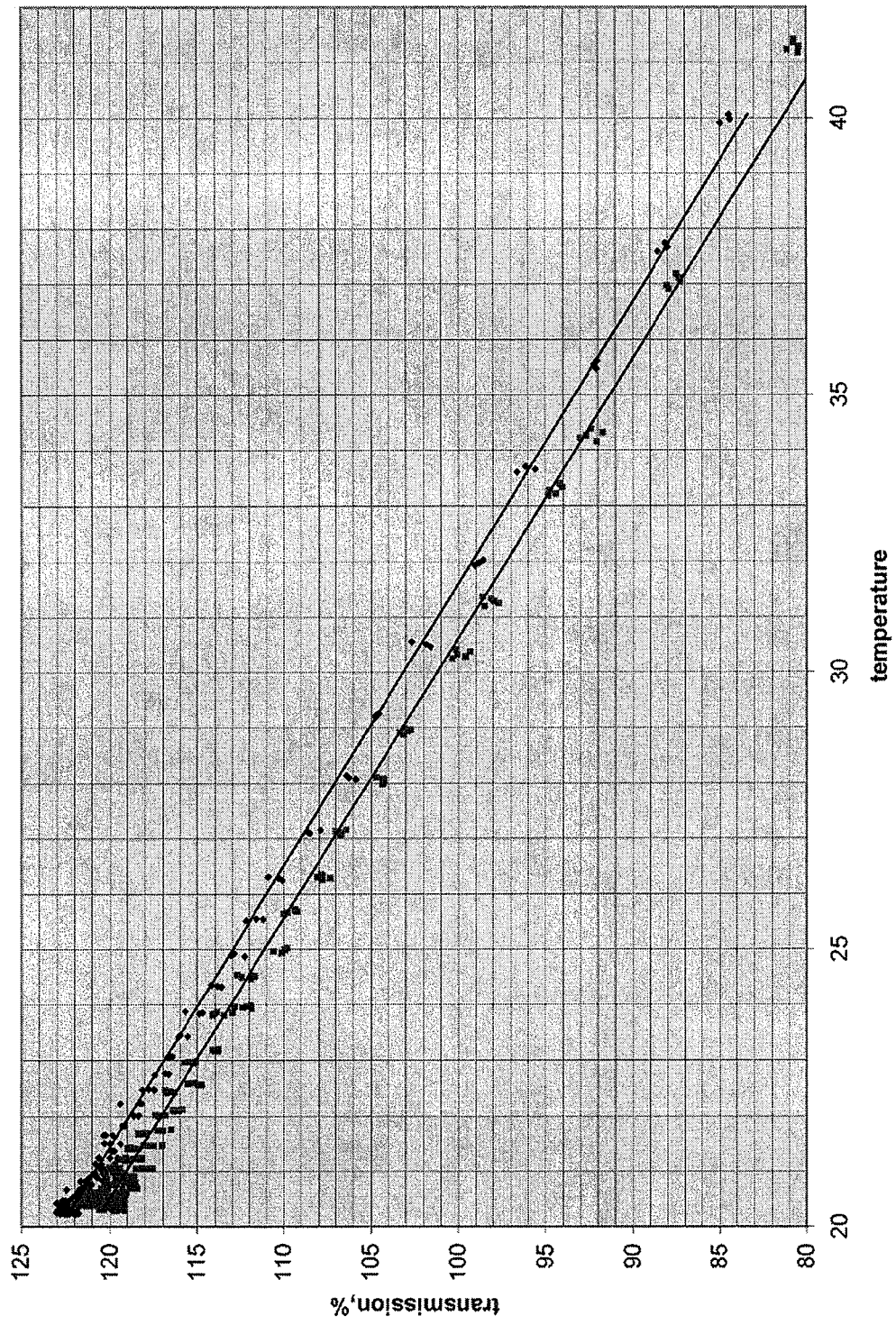
FIG. 7 is an example plot of the temperature dependence of transmission measurements for water and for a water/glucose mixture.

FIG. 7 is a plot of the temperature dependence of transmission measurements for water and for a water/glucose mixture. The measurements of FIG. 7 were taken by transmitting light having a wavelength of 1160 nanometers through a cuvette having a pathlength of about 25 millimeters containing either distilled water (shown as square datapoints) or distilled water having a known concentration (250 milligrams in 1 deciliter of distilled water) of glucose (shown as circular datapoints) at various temperatures.

As shown by FIG. 7, the measured near-infrared transmission varies significantly with varying temperature of the liquid. The measured datapoints for the distilled water and for the water/glucose mixture can both be generally fit with linear functions, which are shown in FIG. 7 as solid lines. These linear functions are generally offset from one another by a temperature of about 2 degrees Celsius. For example, the measured transmission through the distilled water at a temperature of 30 degrees Celsius is approximately equal to the measured transmission through the water/glucose mixture at a temperature of 32 degrees Celsius. Thus, the measured near-infrared transmission alone is insufficient information for determining the glucose concentration of the material being probed. In particular, to measure glucose concentration in blood to a tolerance of 10 milligrams/deciliter or better, the temperature is advantageously measured to an accuracy of 0.05 degrees Celsius or better. Such results highlight the importance of accurately accounting for the temperature of the material being probed by the light in using near-infrared optical measurements (e.g., absorption, transmission) to accurately determine the concentration of a substance (e.g., glucose) in the material.

In certain embodiments in which a portion of the subject's body is probed, the temperature of the portion being probed is directly measured (e.g., either non-invasively or invasively) using a temperature detector (e.g., a thermocouple, a thermistor, an infrared detector (e.g., a thermopile), or any other type of thermometer known to persons of skill in the art). In certain other embodiments, the temperature of the portion being probed is not measured, but measurements of other parameters (e.g., other temperatures) which are expected to be indicative of the temperature of the portion being probed are used instead. For example, for optical measurements made from the subject's eye, the temperature of the subject's eye can be useful for determining the glucose concentration to a desired precision. However, in certain embodiments in which measurements of the temperature of the subject's eye may be impractical to obtain, the subject's body temperature and the ambient temperature can be measured instead and used to account for the temperature dependence of the optical measurements.

Figure 8:
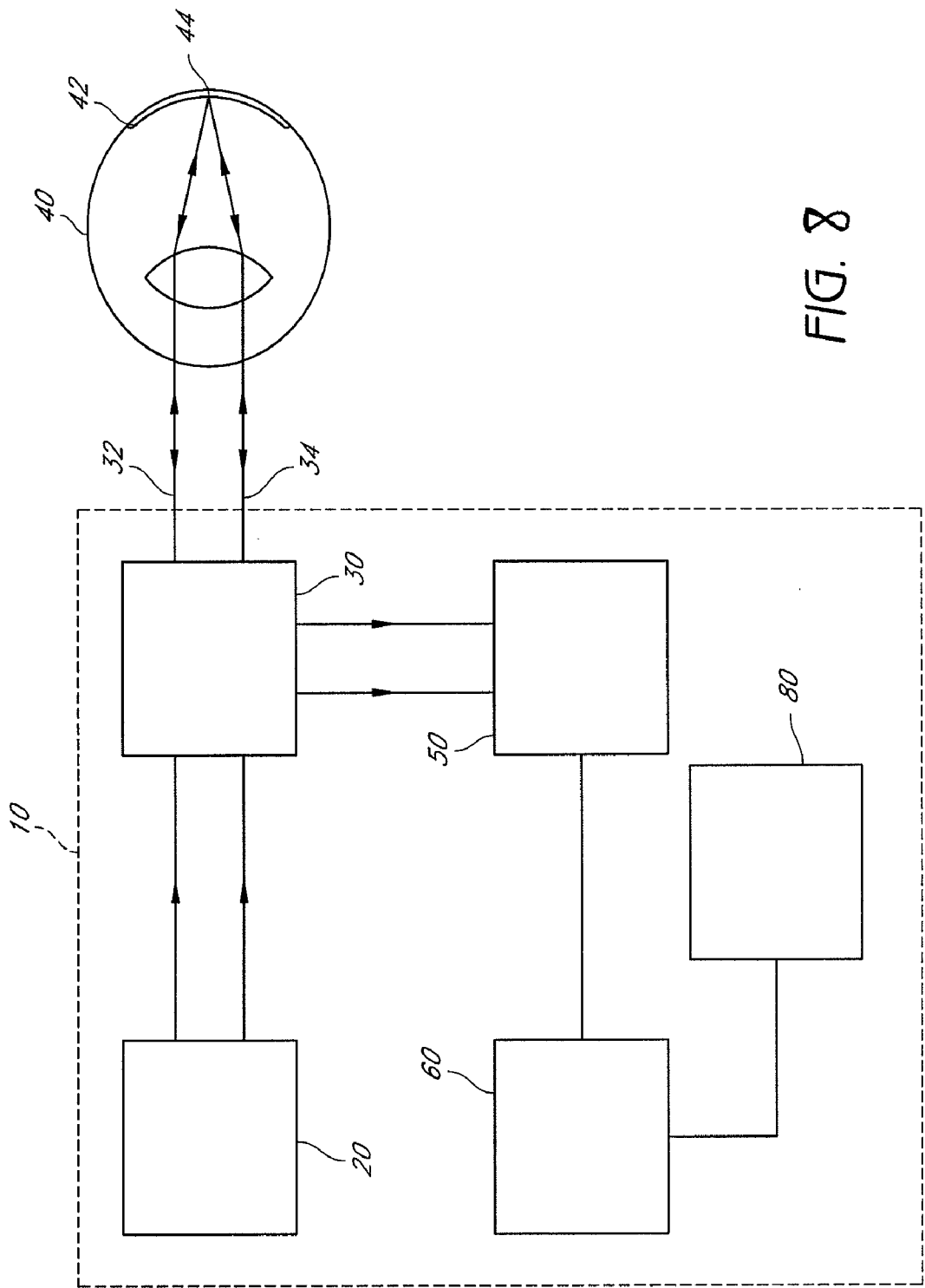
FIG. 8 schematically illustrates another example configuration of an apparatus in accordance with certain embodiments described herein.

FIG. 8 schematically illustrates another example apparatus 10 in accordance with certain embodiments described herein. While this example apparatus 10 is described in conjunction with optical absorption measurements made from the subject's eye, persons skilled in the art recognize that certain embodiments described herein can be used as well with other types of near-infrared optical measurements taken from other portions of the subject's body. For example, other near-infrared optical measurements which can be improved in accordance with certain embodiments described herein include, but are not limited to, transmission measurements, reflection measurements, scattering measurements, polarization measurements, and Raman measurements. In certain embodiments, these measurements are taken from other portions of the subject's body besides the eye, including, but not limited to, skin, earlobe, finger (web or cuticle), lip, or cheek.

In certain embodiments, the apparatus 10 comprises at least one light source 20, an optical system 30, a detector system 50, at least one temperature detector 80, and a computing system 60. The at least one light source 20 (e.g., a first light source 21 and a second light source 22) of certain embodiments is configured to generate light having a first wavelength and light having a second wavelength different from the first wavelength. Various configurations of the at least one light source 20 described herein are compatible with the example apparatus 10 of FIG. 8.

In certain embodiments, the optical system 30 is configured to direct at least one light beam towards a portion of the subject's body. For example, the optical system 30 of certain embodiments is configured to direct at least a portion of the light having the first wavelength towards the subject's eye 40 as a measurement light beam 32 having a first power, wherein at least a portion of the measurement light beam 32 retro-reflects from the subject's retina 42. The optical system 30 of certain embodiments is further configured to direct at least a portion of the light having the second wavelength towards the subject's eye 40 as a reference light beam 34 having a second power, wherein at least a portion of the reference light beam 34 retro-reflects from the subject's retina 42. In certain embodiments, the measurement light beam 32 is a nearly parallel beam and the reference light beam 34 is a nearly parallel beam. Various configurations of the optical system 30 described herein are compatible with the example apparatus 10 of FIG. 8.

In certain embodiments, the apparatus 10 further comprises a detector system 50 configured to receive at least a portion of the at least one light beam after the at least one light beam has interacted with the portion of the subject's body and to generate at least one corresponding signal. For example, in certain embodiments, the detector system 50 is configured to receive the retro-reflected portion of the measurement light beam 32 and the retro-reflected portion of the reference light beam 34. The detector system 50 of certain embodiments is configured to respond to the received retro-reflected portion of the measurement light beam 32 by generating a first signal indicative of the power of the received retro-reflected portion of the measurement light beam 32. The detector system 50 of certain embodiments is configured to respond to the received retro-reflected portion of the reference light beam 34 by generating a second signal indicative of the power of the received retro-reflected portion of the reference light beam 34. Various configurations of the detector system 50 described herein are compatible with the example apparatus 10 of FIG. 8.

In certain embodiments, the apparatus 10 further comprises at least one detector of one or more temperature-indicative parameters corresponding to a temperature of the portion of the subject's body, and is configured to generate at least one signal corresponding to measured values of the one or more temperature-indicative parameters. For example, in certain embodiments, the apparatus 10 comprises at least one temperature detector 80 configured to measure at least one of a body temperature of the subject and an ambient temperature of the subject. The at least one temperature detector 80 is further configured to generate at least one signal indicative of the at least one of the body temperature of the subject and the ambient temperature of the subject. In certain embodiments, the at least one temperature detector 80 can comprise a thermocouple, a thermistor, an infrared detector (e.g., a thermopile), or another type of thermometer known to persons of skill in the art. In certain embodiments, the at least one temperature detector 80 measures temperature to an accuracy of 0.05 degree Celsius or better.

In certain embodiments, the at least one temperature detector 80 is configured to measure both a body temperature of the subject and an ambient temperature of the subject. In certain embodiments, the measurement of the at least one of the body temperature and the ambient temperature is performed concurrently with detecting the power of the retro-reflected portion of the measurement light beam 32 or with detecting the retro-reflected portion of the reference light beam 34. In certain embodiments, the measurement of the at least one of the body temperature and the ambient temperature is performed concurrently with both detecting the power of the retro-reflected portion of the measurement light beam 32 and with detecting the retro-reflected portion of the reference light beam 34.

As used herein, the term "body temperature" has its broadest reasonable meaning, including but not limited to, a temperature of at least a portion of the subject's body. For example, in certain embodiments, the body temperature can be the subject's oral temperature, temporal artery or forehead temperature, eardrum temperature, earlobe temperature, finger temperature, skin temperature, or axillary temperature. In certain embodiments, the body temperature is measured from the same portion of the subject's body from which the optical measurements are made. In certain other embodiments, the body temperature is measured from a portion of the subject's body spaced from the portion of the subject's body from which the optical measurements are made. As used herein, the term "ambient temperature" has its broadest reasonable meaning, including but not limited to, a temperature of a region in proximity to the subject or generally surrounding the subject. For example, in certain embodiments, the ambient temperature can be the room temperature of the room in which the subject is located, the temperature in a region containing the apparatus 10 and the subject, or the temperature within two meters of the subject. The body temperature and the ambient temperature of certain embodiments are parameters which are indicative of the temperature of the portion of the subject's body from which the optical measurements are being made. Thus, in certain embodiments, the body and ambient temperatures are used as proxies for the temperature of the portion of the subject's body (e.g., subject's eye) from which the optical measurements are being made.

In certain embodiments, the apparatus 10 further comprises a computing system 60 configured to receive the first signal, the second signal, and the at least one signal. For example, the computing system 60 can comprise one or more inputs configured to receive the first signal, the second signal, and the at least one signal. In certain embodiments, the one or more inputs of the computing system 60 are also configured to receive a signal indicative of the power of the measurement light beam 32 incident on the subject's eye 40 and to receive a signal indicative of the power of the reference light beam 34 incident on the subject's eye 40.

The computing system 60 of certain embodiments is configured to calculate a value of an optically-measured parameter indicative of the interaction of the at least one light beam with the portion of the subject's body. For example, in certain embodiments, the computing system 60 comprises an electric circuit which is configured to calculate a first ratio of the first power and the power of the retro-reflected portion of the measurement light beam 32, to calculate a second ratio of the second power and the power of the retro-reflected portion of the reference light beam 34, to calculate a parameter dependent on the first ratio and the second ratio (e.g., a difference between the first ratio and the second ratio or a difference between a logarithm of the first ratio and a logarithm of the second ratio), and to determine a concentration of the substance in the subject's blood in response to the calculated parameter and to the at least one signal. Various configurations of the computing system 60 described herein are compatible with the example apparatus 10 of FIG. 6.

When using the near-infrared wavelengths to measure the concentration of substances in the eye, the absorption due to water and possibly other substances can affect the measurements. In order to determine the desired concentration, certain embodiments described herein advantageously separate the absorption due to the substance of interest from the absorption due to other materials, mainly water. Certain embodiments described herein utilize light having one or more wavelengths that are absorbed primarily by water and the substance of interest (e.g., glucose). Certain embodiments described herein take into account that a second substance will have an absorption in a region of wavelengths close to or the same as the region of wavelengths absorbed by the substance of interest.

In certain embodiments, $I_0(\lambda)$ is defined as the power of the light beam having wavelength $\lambda$ incident on the subject's eye 40 (e.g., as measured by the detector system 50), and $I_R(\lambda)$ is defined as the power of the retro-reflected light beam having wavelength $\lambda$ received from the subject's eye (e.g., as measured by the detector system 50). The retro-reflected power $I_R(\lambda)$ can be expressed as:

$$I_R(\lambda) = R \cdot I_0(\lambda) \cdot e^{-\alpha(\lambda, c) \cdot x} \qquad (1)$$

where R is an optical coefficient that includes the parameters that influence the retro-reflected power at the time of the measurement (e.g., reflectivity of the retina at wavelength $\lambda$, the size of the pupil, etc.), $\alpha(\lambda, c)$ is the absorption coefficient of the substance (e.g., glucose) as a function of wavelength $\lambda$ and concentration c, and x is the optical pathlength through the material that contains the substance. This relation can be used to express the transmittance $T_\lambda$ as:

$$T_\lambda = \ln\left(\frac{I_R(\lambda)}{I_0(\lambda)}\right) - \ln(R) = -\alpha(\lambda, c) \cdot x \qquad (2)$$

To find the parameter that is to be correlated to the concentration of the substance (e.g., glucose), the absorption due to water is separated from the total absorption. The wavelength $\lambda_1$ is defined as the wavelength of light which is absorbed by both the substance and water, and the wavelength $\lambda_2$ is defined as the wavelength of light which is absorbed by water but not by the substance. The transmittance at these two wavelengths can be expressed as:

$$T_{\lambda_1} = \ln\left(\frac{I_R(\lambda_1)}{I_0(\lambda_1)}\right) - \ln(R) = (-\alpha(\lambda_1, c) \cdot x + \beta(\lambda_1) \cdot x) \qquad (3)$$

$$T_{\lambda_2} = \ln\left(\frac{I_R(\lambda_2)}{I_0(\lambda_2)}\right) - \ln(R) = \beta(\lambda_2) \cdot x \qquad (4)$$

where $\beta$ is the absorption coefficient of water. Persons skilled in the art would recognize that logarithms in other bases (e.g., base 10) are also compatible with certain embodiments described herein.

The parameter $T_f$ is defined as the difference between the transmittance at the two wavelengths of Equations (3) and (4), and can be expressed as:

$$\begin{aligned} T_f &= T_{\lambda_1} - T_{\lambda_2} \\ &= \ln\left(\frac{I_R(\lambda_1)}{I_0(\lambda_1)}\right) - \ln\left(\frac{I_R(\lambda_2)}{I_0(\lambda_2)}\right) \\ &= -x \cdot (\Delta\beta(\lambda_1, \lambda_2) + \alpha(\lambda_1, c)) \end{aligned} \qquad (5)$$

where $\Delta\beta(\lambda_1, \lambda_2) = \beta(\lambda_1) - \beta(\lambda_2)$, which is a constant.

In deriving Equation (5), the parameter ln(R) was eliminated by subtracting the transmittance at the wavelength $\lambda_2$ from the transmittance at the wavelength $\lambda_1$. This subtraction is advantageously made when the parameter ln(R) is stable in the wavelength region of $\lambda_1$ to $\lambda_2$, such as when $\lambda_1$ and $\lambda_2$ are close to one another (e.g., differing by less than 0.2 microns). In certain embodiments, the value of $\Delta\beta(\lambda_1, \lambda_2)$ is selected to be small (e.g., by selecting the two wavelengths to have similar water absorption coefficients), in order to have a small amount of noise in the measurements.

In certain embodiments, the parameter $T_f$ is calculated by the computing system 60 from the measured powers of the incident light beams and the retro-reflected light beams, and is correlated to the concentration of the substance (e.g., glucose) by accessing and referring to a previously-obtained correlation of the difference $T_f$ and other non-invasively measured parameters (e.g., body temperature, ambient temperature) to clinically accepted invasive measurements. In certain embodiments, the resulting determination of the concentration of the substance in the subject's blood is stored in the memory, is displayed on the display, or both.

In certain embodiments, the computing system 60 is further configured to access an empirical correlation of the optically-measured parameter and the one or more temperature-indicative parameters to concentrations of the substance in blood. For example, in certain embodiments, the computing system 60 accesses one or more previously-determined correlations (e.g., stored in memory) of similar absorption measurements taken from a person's body (e.g., the eye) with empirical or clinical invasive measurements of the concentration of the substance (e.g., glucose) in the person's blood.

In certain embodiments, the computing system 60 is further configured to obtain a concentration of the substance in the subject's blood using the empirical correlation. The obtained concentration corresponds to the value of the optically-measured parameter and the values of the one or more temperature-indicative parameters. For example, in certain embodiments, the computing system 60 uses the previously-determined correlation to equate or correlate the absorption measurements taken from the subject's body (e.g., the eye) to concentrations of the substance of interest in the subject's blood. In certain such embodiments, these calculations also include previously-determined correlations of other non-invasively measured parameters (e.g., body temperature, ambient temperature) with the empirical or clinical invasive measurements, and these other measured parameters, along with the absorption measurements taken from the subject's body, are used to determine the concentration of the substance of interest in the subject's blood. Other examples of non-invasively measured temperature-indicative parameters which can be used in certain embodiments described herein include, but are not limited to, ambient humidity and air flow in a region near the portion of the subject's body (e.g., the eye) from which the optical measurements are being made.

Figure 9:
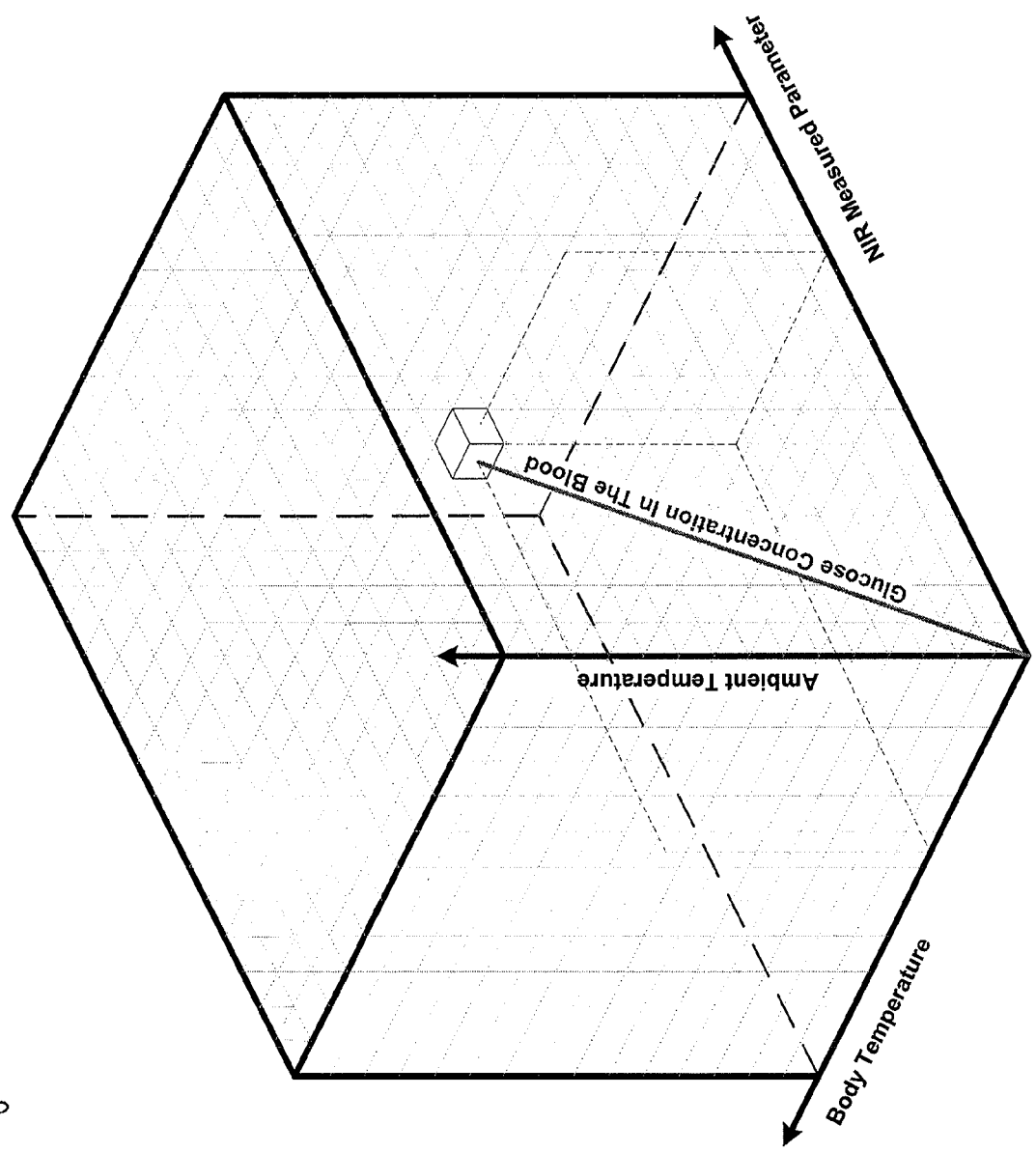
FIG. 9 schematically illustrates an example multi-parameter look-up table in accordance with certain embodiments described herein.

In certain embodiments, at least a portion of the correlation is stored in the memory of the apparatus 10 in the form of a look-up table which relates the concentration of the substance in a person's blood to values of the optically measured parameter (e.g., the difference $T_f$) and the other non-invasively measured parameters (e.g., body temperature, ambient temperature). FIG. 9 schematically illustrates an example multi-parameter look-up table in accordance with certain embodiments described herein. The measured body temperature, the measured ambient temperature, and the optically measured parameter provide three coordinates to a location in the three-dimensional parameter space represented by the look-up table. This location contains a previously empirically-derived value of the concentration of the substance (e.g., glucose) corresponding to the values of these three coordinates. While FIG. 9 schematically illustrates a three-dimensional parameter space, certain other embodiments utilize a parameter space with more than three dimensions. For example, air flow can be used in certain embodiments as a fourth coordinate which is used to specify a location in the parameter space containing a value of the concentration of the substance corresponding to the values of the measured body temperature, measured ambient temperature, measured air flow, and optically measured parameter.

In certain embodiments, at least a portion of the correlation is stored in the memory of the apparatus 10 in the form of one or more formulae which relates the concentration of the substance in a person's blood to values of the difference $T_f$ and the other non-invasively measured parameters (e.g., body temperature, ambient temperature). For example, in certain embodiments, the correlation can be stored as a plurality of linear formulae which interpolate between empirical values of the non-invasively measured parameters to provide estimates of the concentration of the substance.

In certain embodiments, the correlation is an empirical correlation which is the result of a previously-performed study of invasive measurements of the concentrations of the substance in the blood of members of a study group with the non-invasive measurements of the difference $T_f$ and the other non-invasively measured parameters (e.g., body temperature, ambient temperature). For example, the invasive measurements can comprises glucose concentration measurements of blood samples extracted from the members of the study group and these invasive measurements can be correlated with substantially concurrent non-invasive measurements of the difference $T_f$ and the other non-invasively measured parameters (e.g., body temperature, ambient temperature) taken from the members of the study group. In certain embodiments, the empirical study includes measurements from a statistically representative group of people selected to represent a larger population of people for whom concentration measurements are to be made. The group of people in certain embodiments can include both male and female individuals of various ages, weights, and having various physical conditions (e.g., diabetic and non-diabetic individuals). In certain embodiments, the empirical study includes measurements made from these people under a wide variety of conditions. For example, the optically measured parameter, the temperature-indicative parameters (e.g., the body temperature and the ambient temperature), and the invasively-measured concentration are measured over a range of ambient temperatures for which the system is anticipated to be used (e.g., 16 degrees Celsius to 36 degrees Celsius). In certain embodiments, the optically measured parameter, the temperature-indicative parameters, and the invasively-measured concentration are measured over ranges of other variables (e.g., times of day, intervals before and after meals) in order to provide a large database from which correlations of the invasively-measured concentration with the optically measured parameter and the temperature-indicative parameters can reliably be obtained. Thus, the study can be used to provide the correlation of the substance in a person's blood to values of the optically-measured parameter indicative of the concentration of the substance (e.g., the difference $T_f$) and the other non-invasively measured parameters (e.g., body temperature, ambient temperature). In certain embodiments, a look-up table comprising at least a portion of the resultant correlation can be stored in a computer-readable medium (e.g., read-only memory, dynamic random-access memory, flash memory, hard disk drive, compact disk, digital video disk). In certain embodiments, one or more formulae comprising at least a portion of the resultant correlation can be stored in a computer-readable medium.

The results of these measurements in certain embodiments are averaged to provide a correlation representative of an average individual. In certain embodiments, the probability distribution of the values from the group can have a sufficiently large standard deviation, indicating that there are significant variations among individuals. In certain such embodiments, the apparatus can be individually calibrated to a particular subject from whom the optical measurements of the concentration of the substance are to be made. For example, in certain embodiments, an invasive measurement (e.g., a blood droplet glucose measurement) from a subject is used to calibrate subsequent non-invasive optical determinations of the concentration of the substance. Such an invasive measurement from the particular subject can be used to normalize the results obtained from that subject to the average correlation (e.g., by providing a normalization factor in the formula). For example, a measurement of a glucose concentration of 120 mg/dl made from a subject under conditions for which the expected measurement made from an average individual would be 100 mg/dl, a factor of 1.2 can be used to normalize the subsequent determinations of the glucose concentration of the subject. In this way, certain embodiments advantageously provide periodic non-invasive measurements of the concentration while reducing the number of invasive measurements that would otherwise be needed.

In certain embodiments, additional substances with absorptions at the wavelengths used can be accounted for by utilizing additional measurements at additional wavelengths. These measurements are then used with additional equations similar to those described above to determine the unknown values.

Although the invention has been described in terms of certain embodiments, other embodiments that are apparent to those of ordinary skill in the art, including embodiments which do not provide all of the features and advantages set forth herein, are also within the scope of this invention. Accordingly, the scope of the invention is defined by the claims that follow.

What is claimed is:

1. A method of determining the concentration of a substance in a subject's blood, the method comprising:

noninvasively irradiating an eye of the subject with a measurement light beam having a first wavelength and a first power, wherein at least a portion of the measurement light beam is retro-reflected from the retina of the eye, thereby producing a measurement retro-reflected light beam having the first wavelength;

noninvasively irradiating the eye of the subject with a reference light beam having a second wavelength and a second power, the second wavelength different from the first wavelength, wherein at least a portion of the reference light beam is retro-reflected from the retina of the eye, thereby producing a reference retro-reflected light beam having the second wavelength;

measuring at least one of a body temperature of the subject and an ambient temperature of the subject;

detecting a power of the measurement retro-reflected light beam;

detecting a power of the reference retro-reflected light beam;

calculating a measurement ratio of the detected power of the measurement retro-reflected light beam and the first power;

calculating a reference ratio of the detected power of the reference retro-reflected light beam and the second power;

calculating a parameter dependent on the measurement ratio and the reference ratio, wherein the parameter comprises a difference between the measurement ratio and the reference ratio; and determining a concentration of the substance in the subject's blood in response to the calculated parameter and to the at least one of the body temperature and the ambient temperature.

2. The method of claim 1, wherein the substance comprises glucose.

3. The method of claim 1, wherein the measurement light beam is a nearly parallel light beam and the reference light beam is a nearly parallel light beam.

4. The method of claim 3, wherein the measurement light beam and the reference light beam are substantially parallel to one another.

5. The method of claim 1, wherein the first wavelength and the second wavelength are near-infrared wavelengths.

6. The method of claim 1, wherein the first wavelength is in a range between about 920 nanometers and about 980 nanometers and the second wavelength is in a range between about 800 nanometers and about 905 nanometers.

7. The method of claim 1, wherein the first wavelength and the second wavelength differ by less than 0.2 micron.

8. The method of claim 1, wherein measuring at least one of the body temperature and the ambient temperature comprises measuring both the body temperature and the ambient temperature.

9. The method of claim 1, further comprising accessing a correlation of a concentration of the substance in a person's blood to values of the parameter and of the at least one of a body temperature of the person and an ambient temperature of the person.

10. The method of claim 9, wherein accessing the correlation comprises accessing a look-up table relating the concentration of the substance in a person's blood to values of the parameter and of the at least one of a body temperature of the person and an ambient temperature of the person.

11. The method of claim 9, wherein accessing the correlation comprises accessing one or more formulae relating the concentration of the substance in a person's blood to values of the parameter and of the at least one of a body temperature of the person and an ambient temperature of the person.

12. The method of claim 1, wherein the parameter comprises a difference between a logarithm of the measurement ratio and a logarithm of the reference ratio.

13. The method of claim 1, wherein the detector system receives mainly the retro-reflected portions of the measurement light beam and the reference light beam while avoiding receiving other reflections from the subject's eye.

14. An apparatus for measuring a concentration of a substance in a subject's blood, the apparatus comprising:

at least one light source generating light having a first wavelength and generating light having a second wavelength, the second wavelength different from the first wavelength;

an optical system directing at least a portion of the light having the first wavelength towards the subject's eye as a measurement light beam having a first power, at least a portion of the measurement light beam retro-reflecting from the subject's retina, the optical system directing at least a portion of the light having the second wavelength towards the subject's eye as a reference light beam having a second power, at least a portion of the reference light beam retro-reflecting from the subject's retina;

a detector system receiving the retro-reflected portion of the measurement light beam and the retro-reflected portion of the reference light beam, the detector system responsive to the received retro-reflected portion of the measurement light beam by generating a first signal indicative of the power of the received retro-reflected portion of the measurement light beam, the detector system responsive to the received retro-reflected portion of the reference light beam by generating a second signal indicative of the power of the received retro-reflected portion of the reference light beam;

at least one temperature detector measuring at least one of a body temperature of the subject and an ambient temperature of the subject and generating at least one signal indicative of the at least one of the body temperature and the ambient temperature; and a computing system receiving the first signal, the second signal, and the at least one signal, the computing system calculating a first ratio of the first power and the power of the received retro-reflected portion of the measurement light beam, calculating a second ratio of the second power and the power of the received retro-reflected portion of the reference light beam, calculating a parameter dependent on the first ratio and the second ratio, wherein the parameter comprises the difference between the first ratio and the second ratio, and determining a concentration of the substance in the subject's blood in response to the calculated parameter and to the at least one signal.

15. The apparatus of claim 14, wherein the substance comprises glucose.

16. The apparatus of claim 14, wherein the measurement light beam is substantially parallel to the reference light beam.

17. The apparatus of claim 14, wherein the first wavelength and the second wavelength are near-infrared wavelengths.

18. The apparatus of claim 14, wherein the first wavelength is in a range between about 920 nanometers and about 980 nanometers and the second wavelength is in a range between about 800 nanometers and about 905 nanometers.

19. The apparatus of claim 14, wherein the first wavelength and the second wavelength differ by less than 0.2 micron.

20. The apparatus of claim 14, wherein the computing system comprises a central processing unit (CPU), a memory, and a display.

21. The apparatus of claim 20, wherein the memory comprises a correlation of a concentration of the substance in a person's blood to values of the parameter and of the at least one of a body temperature of the person and an ambient temperature of the person.

22. The apparatus of claim 21, wherein the correlation comprises a look-up table relating concentrations of the substance in a person's blood to values of the parameter and of the at least one of a body temperature of the person and an ambient temperature of the person.

23. The apparatus of claim 21, wherein the correlation comprises one or more formulae relating concentrations of the substance in a person's blood to values of the parameter and of the at least one of a body temperature of the person and an ambient temperature of the person.

24. The apparatus of claim 14, wherein the parameter comprises a difference between a logarithm of the first ratio and a logarithm of the second ratio.

25. A computing system for measuring a concentration of a substance in a subject's blood, the computing system comprising:
   one or more inputs configured to receive:
      a first signal indicative of a first power of a measurement light beam incident on a subject's eye, the measurement light beam having a first wavelength;
      a second signal indicative of a second power of a reference light beam incident on a subject's eye, the reference light beam having a second wavelength different from the first wavelength;
      a third signal indicative of a third power of a portion of the measurement light beam retro-reflected from the subject's retina;
      a fourth signal indicative of a fourth power of a portion of the reference light beam retro-reflected from the subject's retina; and
      at least one signal indicative of at least one of a body temperature of the subject and an ambient temperature of the subject; and
   an electric circuit configured to calculate a first ratio of the first power and the third power, to calculate a second ratio of the second power and the fourth power, to calculate a parameter dependent on the first ratio and the second ratio, wherein the parameter comprises a difference between the first ratio and the second ratio, and to determine a concentration of the substance in the subject's blood in response to the calculated parameter and to the at least one of a body temperature of the subject and an ambient temperature of the subject.

26. The computing system of claim 25, further comprising a look-up table relating concentrations of the substance in a person's blood to values of the parameter and of the at least one of a body temperature of the person and an ambient temperature of the person.

27. The computing system of claim 25, further comprising one or more formulae relating concentrations of the substance in a person's blood to values of the parameter and of the at least one of a body temperature of the person and an ambient temperature of the person.

28. The computing system of claim 25, wherein the parameter comprises a difference between a logarithm of the first ratio and a logarithm of the second ratio.

* * * * *